US 6,740,067 B2

(12) United States Patent
Leise, Jr. et al.

(10) Patent No.: US 6,740,067 B2
(45) Date of Patent: *May 25, 2004

(54) REFORMABLE CONVEX ADAPTER FOR OSTOMY APPLIANCE

(75) Inventors: Walter F. Leise, Jr., Lindenhurst, IL (US); Ronald S. Botten, Gurnee, IL (US); Michael A. Metz, Chicago, IL (US)

(73) Assignee: Hollister Incorporated, Libertyville, IL (US)

(*) Notice: Subject to any disclaimer, the term of this patent is extended or adjusted under 35 U.S.C. 154(b) by 18 days.

This patent is subject to a terminal disclaimer.

(21) Appl. No.: 10/279,396

(22) Filed: Oct. 24, 2002

(65) Prior Publication Data

US 2003/0073965 A1 Apr. 17, 2003

Related U.S. Application Data

(63) Continuation-in-part of application No. 09/593,549, filed on Jun. 14, 2000, now Pat. No. 6,569,134.

(51) Int. Cl.⁷ ............................................. A61F 5/44
(52) U.S. Cl. ...................................... 604/332; 604/336
(58) Field of Search ................................. 604/327–343

(56) References Cited

U.S. PATENT DOCUMENTS

| | | | | |
|---|---|---|---|---|
| 3,302,647 A | * | 2/1967 | Marsan ...................... 604/336 |
| 3,898,990 A | | 8/1975 | Nolan ......................... 128/283 |
| 4,213,458 A | | 7/1980 | Nolan et al. ................. 128/283 |
| 4,219,023 A | | 8/1980 | Galindo ....................... 128/283 |
| 4,367,732 A | | 1/1983 | Poulsen et al. .............. 128/156 |
| 4,710,182 A | | 12/1987 | Bryson ........................ 604/339 |
| 4,834,731 A | | 5/1989 | Nowak et al. ............... 604/339 |
| 5,004,464 A | | 4/1991 | Leise, Jr. et al. ............ 604/338 |
| 5,147,340 A | | 9/1992 | Lavender .................... 604/344 |
| 5,163,930 A | | 11/1992 | Blum .......................... 604/338 |
| 5,167,651 A | | 12/1992 | Leise, Jr. et al. ............ 604/339 |
| 5,185,008 A | | 2/1993 | Lavender .................... 604/338 |
| 5,496,296 A | | 3/1996 | Holmberg ................... 604/336 |
| 5,501,678 A | | 3/1996 | Olsen .......................... 604/344 |
| 5,607,413 A | | 3/1997 | Holmberg et al. .......... 604/342 |
| 5,609,585 A | | 3/1997 | Botten et al. ............... 604/332 |
| 5,618,276 A | | 4/1997 | Leise, Jr. et al. ............ 604/336 |
| 5,716,475 A | | 2/1998 | Botten et al. ............... 156/219 |
| 5,730,735 A | | 3/1998 | Holmberg et al. .......... 604/338 |
| 5,811,116 A | | 9/1998 | Gilman et al. .............. 424/443 |
| 5,865,819 A | | 2/1999 | Cisko, Jr. et al. ........... 604/339 |
| 6,093,276 A | | 7/2000 | Leise, Jr. et al. ............ 156/249 |
| 6,569,134 B1 | * | 5/2003 | Leise et al. ................. 604/332 |

OTHER PUBLICATIONS

EP Published application 0 888 760 A1.
UK published application 2 277 031A.
UK published application 2 290 974A.

* cited by examiner

*Primary Examiner*—Glenn K. Dawson
*Assistant Examiner*—Linh Truong
(74) *Attorney, Agent, or Firm*—Marshall, Gerstein & Borun LLP

(57) ABSTRACT

A convex adapter for ostomy appliances is disclosed, the adapter including an adapter ring formed entirely of a soft, tacky, moisture-absorbent and swellable, hydrocolloid-containing adhesive material, one that retains its integrity on hydration and is shape-recoverable when compressive forces are removed, and a thin substantially non-stretchable cover film extending over and beyond the convex bodyside surface of that ring. The film is removably attached to the ring and is preferably transparent (or translucent) so that at least the outline of the ring may be seen through it. A flexible but substantially non-stretchable release sheet is removably attached to the opposite pouchside surface of the ring and may be peeled away from the ring during an initial step in the use of the product.

11 Claims, 1 Drawing Sheet

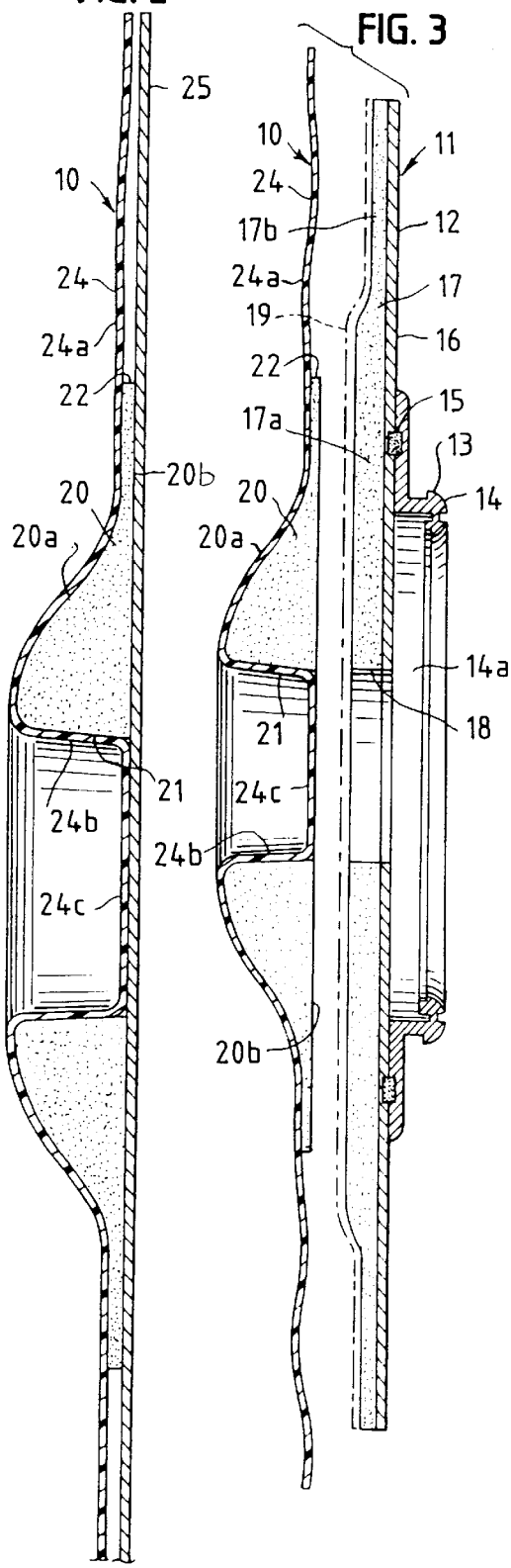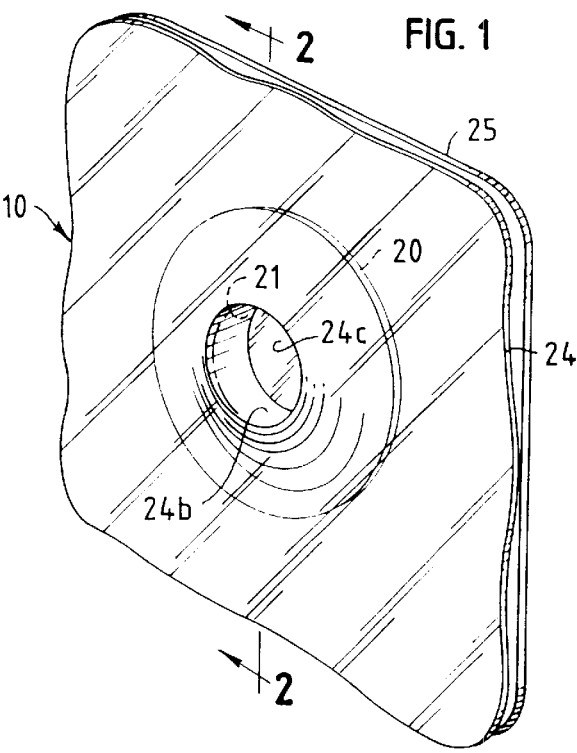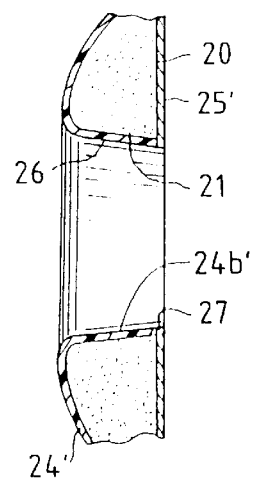

REFORMABLE CONVEX ADAPTER FOR OSTOMY APPLIANCE

RELATED APPLICATION

This application is a continuation-in-part of application Ser. No. 09/593,549, now U.S. Pat. No. 6,569,134, filed Jun. 14, 2000.

BACKGROUND AND SUMMARY

It has long been known to provide ostomy appliances with relatively rigid convex pressure rings for the purpose of increasing stomal protrusion when such an appliance is worn, thereby aiding in the discharge of effluent directly into the pouch and also prolonging the effectiveness of the adhesive seal between the faceplate and peristomal skin surfaces. Reference may be had to U.S. Pat. Nos. 4,834,731, 5,618,276, 5,607,413, 5,730,735 and 5,501,678 for examples of appliances having such pressure rings. It has also been known to provide rigid convex adapters that may be attached to conventional ostomy faceplates as disclosed, for example, in U.S. Pat. Nos. 4,834,731, 5,004,464, 4,219,023, and 5,163,930.

A premise underlying the design of such convex faceplates and adapters is that a patient's stoma is circular in outline, but studies have shown that is not necessarily the case. In one such study it was noted that stomas not only vary widely in size but that only 58% could be considered circular in shape with 42% being regarded as elliptical or irregular. Nordstrom, G. M. et al., *Local Status of the Urinary Stoma—The Relation to Peristomal Skin Complications*, Scand. J. Urol. Nephrol. 24:117–122 (1990). The possibility that a stoma may be non-circular in shape is also noted in European published application 0 888 760 A1, although that application relates to a planar faceplate rather than a convex one. Since convexity has been achieved in the past by providing a faceplate or adapter with a relatively stiff plastic element capable of causing stomal protrusion, such a ring has the capacity of causing considerable wearer discomfort should the opening of the ring fail to match the shape of a wearer's stoma, or should direct contact between such a ring and the wearer's stoma occur when the wearer bends sharply forward, changes positions, or simply moves about.

While it has been known to provide ostomy faceplates with soft, pliant barrier rings, or to supply soft gaskets that may be attached to such rings, such faceplates and gaskets do not function as convex pressure rings. See, for example, U.S. Pat. Nos. 4,213,458 and 4,710,182. Such faceplates/gaskets are commonly formed of a soft flowable material such as karaya, with such material serving as a sealant which flows or is displaced by finger pressure and use into contact with a stoma to prevent leakage and to avoid the excoriating effects that may result if stomal effluent contacts peristomal skin surfaces.

The present invention is concerned with a convex adapter that overcomes the shortcomings of prior convex faceplates and adapters and, specifically, one which may be easily and quickly adjusted in size and shape to match the size and shape of a wearer's stoma. The adapter includes a ring formed entirely of a moisture-absorbing skin barrier material that is adhesive, soft, rubbery, non-distintegrating upon hydration, non-flowing, and shape-recoverable following compressive deformation. To achieve such objectives, the barrier material should have a continuous phase of an elastomeric adhesive blend including a styrene-olefin-styrene rubber, and a discontinuous phase of hydrocolloid particles dispersed throughout the rubbery adhesive phase.

An important aspect of this invention lies in providing the convex surface of the adapter ring of barrier material with a substantially inelastic and non-stretchable cover film that extends outwardly a substantial distance beyond the edges of the ring. The cover film must be removable from the ring and is preferably transparent, or least translucent, so that the rings' outermost edges, and preferably the opening of a faceplate to which the adapter is to be adhered, may be seen through the film. In addition, the opposite surface of the barrier ring is covered by a removable release sheet which, like the cover film, is substantially non-stretchable. The release sheet is preferably of the same size and shape as the cover film, but both should be substantially larger than the faceplate to which the adapter ring is to be attached so as to facilitate removal of the cover film after the faceplate and convex adapter ring had been joined together.

It is well known to provide an adhesive faceplate of an ostomy appliance (either a one-piece appliance or a two-piece appliance) with a small circular starter opening which may then be cut to larger size (with scissors) to match the size and shape of a patient's stoma. Alternatively, the faceplate may be manufactured with an opening sized and shaped (e.g., round or oval-shaped) to approximate the size and shape of a patient's stoma. In either case, the method of use of the convex adapter of this invention may involve reshaping or reforming the adapter ring to match the size and shape of the opening of the faceplate. To that end, a user first strips away the non-stretchable release sheet and then, if the adapter ring sized and shaped to match a patient's stoma, the user places the exposed planar surface of the adapter ring against the faceplate, with the openings of the two parts in register, and then strips away the non-stretchable cover film. Alternatively, and especially where the adapter ring must be stretched and reformed so that its opening substantially matches that of the faceplate opening, a user may first remove both the release sheet and the cover film from the adapter ring and then, gripping the adapter ring between the fingers of both hands, reshape the adapter ring and then adhere it to the faceplate.

Other advantages, features and objects of the invention will become apparent from the specification and drawings.

DRAWINGS

FIG. 1 is a perspective view of a convex adapter as it would be supplied to a user.

FIG. 2 is an enlarged sectional view taken along line 2—2 of FIG. 1.

FIG. 3 is a sectional view similar to FIG. 2 but showing the adapter with its release sheet removed and with the adapter located in proximity to the faceplate of an ostomy appliance (the release sheet of the faceplate also having been removed).

FIG. 4 is a fragmentary sectional view showing a second embodiment in which the cover film and release sheet are cut to provide an opening in register with the stoma-receiving opening of the convex barrier ring.

DETAILED DESCRIPTION OF PREFERRED EMBODIMENTS

Referring to FIGS. 1–3, the numeral 10 generally designates a convex adapter for use within an adhesive faceplate 11 (FIG. 3) of an ostomy appliance. The appliance may be of the one-piece or two-piece type as such terms are commonly used in the art to mean appliances in which an adhesive faceplate is permanently attached to a pouch (one-piece) or one in which a faceplate and pouch are separate components that may be coupled to and uncoupled from each other (two-piece). In the particular construction illustrated in FIG. 3, appliance 11 is a two-piece appliance in which only the adhesive faceplate component 12 of the appliance is depicted. The faceplate includes a coupling ring 13 of a flexible plastic material similar in construction and operation to the male coupling component disclosed in co-owned U.S. Pat. No. 5,185,008, the disclosure of which is incorporated by reference herein. The ring includes a male element 14 adapted to be received in the channel of a mating coupling ring attached to a collection pouch (not shown). The faceplate ring 13 is joined by heat seal 15 to the heat-sealable film 16 of faceplate 12, and a layer 17 of skinfriendly pressure-sensitive adhesive is secured to the bodyside surface of film 16. The adhesive layer 17 and film 16 have a central opening 18 that is generally concentric with the opening 14a of the coupling ring 13.

Opening 18 may be relatively small and serve only as a starter opening that may be cut (with scissors) to match the size and shape of a patient's stoma. Thus, if a stoma is of flattened oval or elliptical shape, a caregiver or patient may enlarge opening 18 so that it matches the outline of the stoma. Alternatively, opening may be precut and presized during manufacture to approximate the size and shape (e.g., circular or oval) of a wearer, it being understood that in such case the manufacturer would offer a line of faceplates having openings of different sizes and shapes.

The adhesive layer 17 may be formed of any suitable pressure-sensitive adhesive commonly used for securing the faceplates of ostomy appliances to the peristomal skin surfaces of a wearer. For example, a hypoallergenic medical-grade acrylic adhesive may be used. However, it is preferable that the adhesive layer be formed of a soft, skinfriendly hydrocolloid-containing adhesive material that is capable of absorbing moisture and has both wet and dry tack. Such a material is commonly referred to as a skin barrier composition and typically comprises a continuous elastomeric adhesive phase having hydrocolloid particles dispersed throughout the continuous phase. Initial tack, usually referred to as "dry tack" is provided by the continuous phase but, because such a composition is occlusive or non-breathable, adherence to the skin would be disrupted by perspiration and by liquid stomal discharge if it were not for the dispersed hydrocolloids which absorb fluids and thereby maintain and possibly enhance adhesive attachment to the skin. U.S. Pat. No. 4,551,490 and other references disclose that suitable water-absorbing and swellable hydrocolloid gums may include sodium carboxymethylcellulose, pectin, gelatin, guar gum, locust bean gum, and the like. The elastomers used in the continuous phase may be polyisobutylene, natural rubber, silicone rubber, acrylonitrile rubber and other elastomers known in the art to have similar properties In the particular faceplate depicted in FIG. 3, the adhesive layer 17 is contoured, having a relatively thick annular inner portion 17a and a thin outer portion 17b although, if desired, layer 17 may instead be of substantially uniform thickness throughout. A protective release sheet 19 formed of silicone-coated paper or other suitable sheet material, shown only in phantom in FIG. 3, covers the bodyside surface of the adhesive layer and is removable from that surface at the time the faceplate is being prepared for use.

In outline, faceplate 12 may be of generally rectangular (square) shape with rounded corners as depicted, for example, in co-owned U.S. Pat. Nos. 5,147,340 and 5,167,651, but other shapes such as circular, oval, or even triangular (see, for example, U.S. Pat. No. 5,811,116) may be provided.

Adapter 10 comprises an adapter ring 20 having a convex bodyside surface 20a and a generally planar pouchside surface 20b. A stoma-receiving opening 21 of generally cylindrical shape extends through the ring. The rings' outermost edge 22 is circular and concentric with stoma-receiving opening 21.

The adapter ring 20 is formed entirely of a soft skin barrier material that is generally non-flowable, retains its integrity upon hydration, and has shape-recovering properties. It should also be compatible, at least for the expected duration of usage, with the adhesive composition 17 of faceplate 12. If the faceplate adhesive 17 is composed of a hydrocolloid-containing skin barrier material, adapter ring 20 may be of similar composition as long as the composition of the ring is flow-resistant, does not disintegrate as it absorbs moisture, and is generally shape-recoverable following compressive deformation. Alternatively, even if the faceplate adhesive 17 is composed of a hydrocolloid-containing skin barrier material, the adapter ring may be formed of a skin barrier material having substantially different properties such as, for example, greater resistance to stomal discharge.

Specifically, the adapter ring 20 should be of a composition consisting essentially of a continuous phase of two or more elastomeric adhesives and a discontinuous phase of hydrocolloid particles dispersed throughout the continuous phase. For flow resistance, shape-recoverability, and the capacity to retain integrity during swelling of the hydrocolloid component upon liquid absorption, the continuous phase includes a physically crosslinked elastomer such as a styrene-olefin-styrene block copolymer as disclosed in co-owned U.S. Pat. No. 5,492,943, the disclosure of which is incorporated by reference herein. The composition of that patent includes a blend of two viscoelastic adhesive elastomers, specifically high molecular weight polyisobutylene and a styrene block copolymer which, along with a plasticizer (preferably petrolatum) and a suitable tackifier and antioxidant, form a continuous phase in which hydrocolloid particles such as sodium carboxymethylcellulose and pectin are dispersed. While the composition of the aforementioned patent is preferred, it is believed that other adhesive barrier compositions containing physically crosslinked elastomers or mixtures of such elastomers, such as those disclosed in U.S. Pat. Nos. 4,231,369 and 4,551,490, might also be used.

The importance of including a styrene-olefin-styrene block copolymer in the blend of materials of the barrier's adhesive phase lies in providing a rubbery constituent that contributes to the barrier material's integrity upon hydration, its non-flowability, its resistance to compressive deformation, and its recoverability following such deformation. At the same time, the barrier material is of sufficient softness and low modulus that pulling forces may be applied by the fingers in opposite directions (in the general plane of the ring) to reform the outline of barrier layer 17 and the shape of the stoma opening extending therethrough, assuming that release sheet 25 and non-stretchable cover sheet 24 have first been removed as described hereinafter.

Preferably, the viscoelastic adhesive phase is a blend of elastomers composed of about 2 to 15% (preferably 3 to 7%) by weight of one or more high molecular weight polyisobutylenes and about 5 to 20% by weight (preferably 17 to 14%) of one or more styrene block copolymers. "High molecular weight" here refers to a polyisobutylene having a viscosity average molecular weight within the range of about 75,000 to 2,350,000 (preferably about 1,000,000 to 1,900,000) as determined from intrinsic viscosity measurements in diisobutylene at 20° C. Such polyisobutylenes are commonly available and are known, for example, under the designations Vistanex MM-L80, MM-L100, MM-L120, and MM-L140 from Exxon Corp., Houston, Tex.

Styrene block copolymer or copolymers suitable for blending with such high molecular weight polyisobutylene (s) may be identified generally as styrene-olefin-styrene block copolymers. Particularly suitable for this purpose are styrene-isoprene-styrene and styrene-butadiene-styrene block copolymers, both of which are commercially available, for example, from Shell Chemical and other suppliers. A styrene-isoprene-styrene block copolymer marketed as Kraton 1107 (Shell Chemical) is believed particularly suitable, but other Kraton copolymers, such as Kraton 1100, 1101, and 1102 are also considered suitable.

Petrolatum may be used advantageously as a hydrocarbon plasticizer component in the adhesive barrier composition, although mineral oil may also be used. In addition, the composition may contain one or more hydrocarbon tackifier resins, such as the aliphatic hydrocarbon resin tackifier commercially available from Hercules Inc. (Wilmington, Del.) as Piccotac 95. Other tackifiers such as trimethylol propane esters of rosin (Staybelite Ester 20 from Hercules) or pentacrythritol esters of rosin (Pentalyn H from Hercules) might also be used. In addition, the barrier composition may include a suitable antioxidant such as Irganox 1010 or Irganox 1076 (Ciba Geigy) or any of a number of other commercially-available antioxidants.

As shown in FIGS. 1 and 2, a thin flexible but non-stretchable cover film 24 covers the convex surface of barrier ring 20 and includes an outer portion 24a that extends outwardly a substantial distance beyond the peripheral edge 22 of ring 20. Film 24 is shown to be generally square in outline, but other shapes may be provided. What is important is that the cover film 24 be flexible and easily removable from the convexly-curved surfaces of the barrier ring. Ideally, the cover film is sufficiently transparent or translucent so that it allows the outermost edge 22 and preferably the opening of a faceplate to which the adapter is to be adhered, to be viewed therethrough.

In the embodiment illustrated in FIGS. 1–3, cover film 24 extends into the opening 21 of barrier ring 20, having a generally cylindrical sleeve portion 24b that extends axially and covers the cylindrical surface of the ring as well as an end portion 24c that bridges the barrier opening along the faceplate-facing end of that opening.

Any of a variety of thin, flexible, and substantially non-stretchable polymeric materials may be used for cover film 24. Polyethylene terephthalate is suitable, as are a number of other stretch-resistant polymeric materials such as for example, polystyrene.

The opposite or pouchside surface 20b of the adapter ring is covered by a removable release sheet 25 that is also substantially non-stretchable and, unlike film 24, may be relatively stiff and opaque. Siliconized paper may be used with the silicone-treated surface being in contact with the ring surface 20b to facilitate removal of the sheet at the time of application. Alternatively, the cover sheet may be composed of a transparent or translucent polymeric material such as, for example, silicone-coated polyethylene terephthalate.

While both the release sheet 25 and the cover film 24 should adhere only weakly to the adhesive adapter ring 20, the forces of adhesion between the cover film 24 and the ring should be greater than those between the ring and the release sheet 25, thereby permitting a user to peel the release sheet away from the pouchside surface of the adapter ring without risking detachment of the adapter ring from its cover film. Similarly, the forces of adhesion between the adapter ring 20 and the adhesive layer 17 of faceplate 12 should be substantially greater than the forces of adhesion between the cover film 24 and the contoured surface of adapter ring 20, thereby permitting the cover film to be peeled away from the adapter ring after that ring has been secured to the faceplate.

The release sheet 25 and cover film 24 are of the same size and shape and have their edges in register, having been cut simultaneously in the same cutting step of a manufacturing procedure that may be of the type described in co-owned U.S. Pat. No. 5,716,475. Thus, if cover film 24 is of generally rectangular shape as shown in FIG. 1, the coextensive release sheet 25 is of the same shape. In that connection, it should be noted that both the release sheet and the cover film are substantially larger than the faceplate 12, each having a marginal portion that projects outwardly more than 0.25 inches, and preferably more than 0.5 inches, beyond the outer edge 22 of the barrier ring 20. Since the outer marginal portions of the cover film and the release sheet are free of adhesive and have non-adhering surfaces, they are easily separated from each other and from the barrier ring.

In the preferred embodiment depicted in FIGS. 1–3 of the drawings, the portion 24c of the cover film disposed within the opening 21 of the adapter ring 20 is in contact with, or in close proximity to, release sheet 25. The embodiment of FIG. 4 is similar to the one already described except that neither cover film 24' nor the release sheet 25' bridges the opening 21 of adapter ring 20. Instead, aligned openings 26 and 27 are provided in cover film 24' and release sheet 25' respectively.

In use of the invention, if the faceplate is of the type having a small starter opening, then a first step involves enlarging that opening with scissors so that it matches the size and shape of the patient's stoma. Thereafter, the protective release sheet 19 is peeled away from the adhesive surface of the faceplate and the release sheet 25, 25' of adapter 10 is similarly removed. If the opening 21 of the barrier ring 20 already matches the size and shape of the opening in the faceplate, then the user may simply bring the opposing surfaces of the barrier ring and faceplate together while the cover film 24, 24' remains attached to the barrier ring. Thereafter, the non-stretchable and removable cover film is peeled away from the barrier ring 20, and the user then secures the faceplate with its convex adapter in place to the skin surfaces surrounding the stoma.

Alternatively, a user may remove not only the release sheet 25, 25' but also the cover film 24, 24' from opposite surfaces of the barrier ring 20 before adhering that barrier ring to the adhesive surface of faceplate 12. Such sequence is particularly appropriate where stretching of the reformable adapter is necessary prior to attachment of the adapter. For example, if the opening of the faceplate has been customized to match the size and shape of a patient's stoma, then a user, after removing both the non-stretchable release sheet 25, 25' and the non-stretchable cover film 24, 24' from the barrier ring 20, may stretch and reform the barrier ring so that its opening 21 conforms with the size and shape of the faceplate's opening.

While in the foregoing we have disclosed embodiments of the invention in considerable detail for purposes of illustration, it will be understood by those skilled in the art that many of these details may be varied without departing from the spirit and scope of the invention.

What is claimed is:

1. A convex adapter for use with an adhesive faceplate of an ostomy appliance, comprising an adapter ring formed entirely of a soft shape-recoverable skin barrier material having a convex bodyside surface, a generally planar opposite surface, and a centrally-located stoma-receiving opening therethrough; a removable release sheet covering said opposite surface; and a substantially non-stretchable and removable cover film covering said convex surface; said barrier material consisting essentially of a continuous phase of an elastomeric adhesive and a discontinuous phase of moisture-absorbing and swellable hydrocolloid particles dispersed therein; said removable cover film being sufficiently transparent for revealing said adapter ring therethrough and having a marginal portion extending outwardly beyond the periphery of said adapter ring.

2. The convex adapter of claim 1 in which said removable release sheet has a marginal portion extending outwardly beyond the periphery of said adapter ring.

3. The convex adapter of claim 2 in which said removable cover film and said removable release sheet are of substantially the same size.

4. The convex adapter of claims 1, 2 or 3 in which said cover film projects outwardly from the periphery of said adapter ring a distance more than 0.25 inches.

5. The convex adapter of claim 4 in which said marginal portion of said removable cover film projects outwardly beyond the periphery of said adapter ring more than 0.5 inches.

6. The convex adapter of claim 2 or 3 in which said marginal portions of said release sheet and said backing film are unsecured to each other.

7. The convex adapter of claims 1, 2 or 3 in which said barrier material consists essentially of a continuous phase of an elastomeric adhesive having a styrene-olefin-styrene copolymer as an ingredient thereof.

8. The convex adapter of claim 7 in which said barrier material is a homogenous blend of a styrene-olefin-styrene copolymer and polyisobutylene for providing said adapter ring with shape recoverability, non-flowability, and retention of integrity on hydration.

9. The convex adapter of claims 1, 2 or 3 in which said cover film extends into said centrally-located stoma-receiving opening of said adapter ring; said stoma-receiving opening having an inner passage-defining surface covered by said cover film.

10. The convex adapter of claim 9 in which said cover film bridges said stoma-receiving opening along the plane of said opposite surface of said adapter ring.

11. The convex adapter of claims 1, 2 or 3 in which said skin barrier material of said adapter ring adheres more strongly to said removable cover film than to said release sheet.

* * * * *